(12) United States Patent
Sargeant (10) Patent No.: US 8,608,775 B2
(45) Date of Patent: Dec. 17, 2013

(54) TWO PART TAPE ADHESIVE FOR WOUND CLOSURE

(75) Inventor: Timothy Sargeant, Guilford, CT (US)

(73) Assignee: Covidien LP, Mansfield, MA (US)

( * ) Notice: Subject to any disclaimer, the term of this patent is extended or adjusted under 35 U.S.C. 154(b) by 177 days.

(21) Appl. No.: 13/346,992

(22) Filed: Jan. 10, 2012

(65) Prior Publication Data
US 2012/0191132 A1    Jul. 26, 2012

Related U.S. Application Data

(60) Provisional application No. 61/435,466, filed on Jan. 24, 2011.

(51) Int. Cl.
*A61B 17/03* (2006.01)

(52) U.S. Cl.
USPC .............................................. 606/215

(58) Field of Classification Search
USPC .............................................. 606/213–216
See application file for complete search history.

(56) References Cited

U.S. PATENT DOCUMENTS

| | | | |
|---|---|---|---|
| 679,993 A * | 8/1901 | Ross et al. ................ 602/75 |
| 2,762,371 A * | 9/1956 | Guio ........................ 606/216 |
| 2,818,865 A * | 1/1958 | Jacoby, Jr. ............... 606/216 |
| 3,124,136 A | 3/1964 | Usher | |
| 3,863,640 A * | 2/1975 | Haverstock ............... 606/216 |
| 4,141,363 A * | 2/1979 | James et al. ............. 606/216 |
| 4,806,614 A | 2/1989 | Matsuda et al. | |
| 4,815,468 A * | 3/1989 | Annand .................... 606/216 |
| 4,983,176 A * | 1/1991 | Cushman et al. ......... 606/151 |
| 5,259,835 A * | 11/1993 | Clark et al. ................ 602/48 |
| 5,334,217 A | 8/1994 | Das | |
| 5,354,336 A | 10/1994 | Kelman et al. | |
| 5,445,597 A * | 8/1995 | Clark et al. ................ 602/48 |
| 5,744,545 A | 4/1998 | Rhee et al. | |
| 5,752,974 A | 5/1998 | Rhee et al. | |
| 6,077,281 A | 6/2000 | Das | |
| 6,329,564 B1 * | 12/2001 | Lebner ...................... 602/41 |
| 6,479,725 B1 | 11/2002 | Brothers | |
| 6,773,699 B1 | 8/2004 | Soltz et al. | |
| 6,833,408 B2 | 12/2004 | Sehl et al. | |

(Continued)

FOREIGN PATENT DOCUMENTS

WO    WO 01/06829    2/2001

OTHER PUBLICATIONS

Huang, et al., "Biotin-Derivatized Poly(L-lysine)-g-poly(ethylene glycol): A Novel Polymeric Interface for Bioaffinity Sensing", *Langmuir*, vol. 18, pp. 220-230 (2002) (published on Web Dec. 5, 2001).

(Continued)

*Primary Examiner* — Ryan Severson (57) ABSTRACT

A wound closure device includes a first applicator including a handle portion and a substrate engaging portion and a second applicator including a handle portion and a substrate engaging portion. A first substrate is releasably couplable to the substrate engaging portion of the first applicator and includes a tissue reactive surface and a self-reactive surface. A second substrate is releasably couplable to the substrate engaging portion of the second applicator and includes a tissue reactive surface and a self-reactive surface. The self-reactive surfaces of the first and second substrates each possess reactive groups known to have complementary functionality for bonding the first and second substrates together.

20 Claims, 3 Drawing Sheets

(56) References Cited

U.S. PATENT DOCUMENTS

| | | |
|---|---|---|
| 6,939,364 B1 | 9/2005 | Soltz et al. |
| 6,969,400 B2 | 11/2005 | Rhee et al. |
| 7,332,641 B2* | 2/2008 | Lebner et al. .................. 602/42 |
| 7,354,446 B2* | 4/2008 | Lebner ........................ 606/213 |
| 7,414,168 B2* | 8/2008 | Lebner ........................ 602/42 |
| 7,594,914 B2* | 9/2009 | Luchetti ...................... 606/41 |
| 7,662,169 B2* | 2/2010 | Wittmann .................... 606/216 |
| 8,469,996 B2* | 6/2013 | Wittmann .................... 606/216 |
| 2002/0029063 A1* | 3/2002 | Wittmann .................... 606/215 |
| 2002/0099315 A1* | 7/2002 | Lebner ........................ 602/54 |
| 2004/0059377 A1* | 3/2004 | Peterson et al. .............. 606/216 |
| 2004/0204740 A1* | 10/2004 | Weiser ........................ 606/213 |
| 2005/0020956 A1* | 1/2005 | Lebner ........................ 602/42 |
| 2005/0020957 A1* | 1/2005 | Lebner ........................ 602/42 |
| 2005/0021081 A1* | 1/2005 | Lebner ........................ 606/215 |
| 2005/0021082 A1* | 1/2005 | Lebner ........................ 606/215 |
| 2005/0021083 A1* | 1/2005 | Lebner ........................ 606/216 |
| 2005/0054771 A1 | 3/2005 | Sehl et al. |
| 2005/0080453 A1* | 4/2005 | Lebner et al. ................. 606/216 |
| 2005/0165445 A1* | 7/2005 | Buckman et al. ............. 606/213 |
| 2005/0281802 A1 | 12/2005 | Gong et al. |
| 2006/0210602 A1 | 9/2006 | Sehl et al. |
| 2006/0241691 A1 | 10/2006 | Wilk |
| 2006/0271104 A1* | 11/2006 | Viola et al. ................... 606/214 |
| 2007/0106327 A1* | 5/2007 | Thill et al. ................... 606/213 |
| 2008/0302487 A1 | 12/2008 | Goodman et al. |
| 2009/0028957 A1 | 1/2009 | Daniloff |
| 2009/0030451 A1 | 1/2009 | Hadba et al. |
| 2009/0044895 A1 | 2/2009 | Fortune et al. |
| 2009/0099579 A1 | 4/2009 | Nentwick et al. |
| 2009/0240186 A1* | 9/2009 | Fang ........................... 602/54 |
| 2009/0270884 A1 | 10/2009 | Hake |
| 2010/0256674 A1* | 10/2010 | Wittmann .................... 606/216 |
| 2012/0095502 A1* | 4/2012 | Bargon et al. ................ 606/216 |
| 2012/0191132 A1* | 7/2012 | Sargeant ...................... 606/214 |

OTHER PUBLICATIONS

European Search Report from EP Appl. No. 07751965 dated Aug. 27, 2012.

* cited by examiner

TWO PART TAPE ADHESIVE FOR WOUND CLOSURE

CROSS-REFERENCE TO RELATED APPLICATION

This application claims the benefit of, and priority to, U.S. Provisional Application No. 61/435,466, filed on Jan. 24, 2011, the entire disclose of which is incorporated by reference herein.

TECHNICAL FIELD

The present disclosure relates to devices for apposing tissue and closing wounds, and in particular, to wound closure devices that align and approximate tissue for uniform wound closure.

BACKGROUND

Techniques for repairing damaged or diseased tissue are widespread in medicine. Wound closure devices, such as sutures, staples, and other repair devices, like mesh or patch reinforcements, are frequently used for repair. In recent years there has developed increased interest in replacing or augmenting sutures with adhesive bonds. The reasons for this increased interest include: the potential speed with which repair might be accomplished; the ability of a bonding substance to effect complete closure, thus preventing seepage of fluids; and the possibility of forming a bond without excessive deformation of tissue.

A wound may be closed by sewing or stapling the edges of the wound together. In the case of deep wounds, the edges may first need to be sewn together layer by layer, placing and leaving some sutures under the skin. Alternatively or additionally, adhesives may be directly applied and used for wound closure purposes.

Approximating tissue, however, with the use of adhesives, staples, and/or sutures may require grasping the tissue adjacent the edges of the wound. The use of forceps or other tissue grasping devices may indent the tissue, evert the wound edges during closure, or fail to provide uniform adhesion in subcutaneous tissue.

Thus, it would be desirable to provide a wound closure device that is easily insertable into a wound and effects uniform and even closure thereof.

SUMMARY

A wound closure device includes a first applicator including a handle portion and a substrate engaging portion and a second applicator including a handle portion and a substrate engaging portion. A first substrate is releasably couplable to the substrate engaging portion of the first applicator and includes a tissue reactive surface and a self-reactive surface. A second substrate is releasably couplable to the substrate engaging portion of the second applicator and includes a tissue reactive surface and a self-reactive surface. The self-reactive surfaces of the first and second substrates each possess reactive groups known to have complementary functionality for bonding the first and second substrates together.

Methods for closing a wound utilizing the wound closure device of the present disclosure are also described. In accordance with the present methods, a first substrate including a tissue reactive surface and a self-reactive surface are introduced into a wound via a first applicator, the first applicator including a handle portion and a substrate engaging portion for releasably engaging the first substrate. A second substrate including a tissue reactive surface and a self-reactive surface is introduced into a wound via a second applicator, the second applicator including a handle portion and a substrate engaging portion for releasably engaging the second substrate. The tissue reactive surfaces of the first and second substrates are applied to tissue within a wound and the self-reactive surfaces of the first and second substrates are contacted with each other for bonding and closing the wound.

BRIEF DESCRIPTION OF THE DRAWINGS

The illustrative embodiments described herein will become more readily apparent from the following description, reference being made to the accompanying drawings in which.

DETAILED DESCRIPTION

Wound closure devices described herein include a one or two piece assembly including two tissue fastening substrates and applicators for applying the same. The tissue fastening substrates each include a tissue reactive surface and a self-reactive surface known to have complementary reactivity to the self-reactive surface of the other tissue fastening substrate. The wound closure devices can be employed to adhere tissue edges, close wounds, seal air/fluid leaks in tissues, and for tissue augmentation such as sealing or filling voids or defects in tissue.

Embodiments of the presently disclosed wound closure device will now be described in detail with reference to the drawing figures wherein like reference numerals identify similar or identical elements. In the following discussion, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is further from the clinician during proper use. As used herein, the term "patient" should be understood as referring to a human subject or other animal, and the term "clinician" should be understood as referring to a doctor, nurse or other care provider and may include support personnel.

Referring now to FIGS. 1A-1B and 2A-2B, there is illustrated an exemplary wound closure device 100 for use in closing a wound. Wound closure device 100 includes two applicators 102. As the two applicators 102 are substantially identical, only one applicator 102 will be described. Applicator 102 includes a handle portion 104 and a substrate engaging portion 106. The handle portion 102 is adapted for grasping by a clinician and for manipulating substrate engaging portion 106. Substrate engaging portion 106 includes tines 106a and 106b which are configured to extend along a length of applicator 102. The tines 106a and 106b may be flexible or rigid depending upon the types of tissue to be approximated and closed. While illustrated as including two tines 106a and 106b, the substrate engaging portion 106 may include a single tine of varying size or more than two tines depending on such factors as the size of the wound and the degree of rigidity required of the substrate engaging portion 106. Similarly, the size and length of the handle portion 104 may vary depending on the depth of the wound and the length of the substrate engaging portion 106.

Figure 1A:
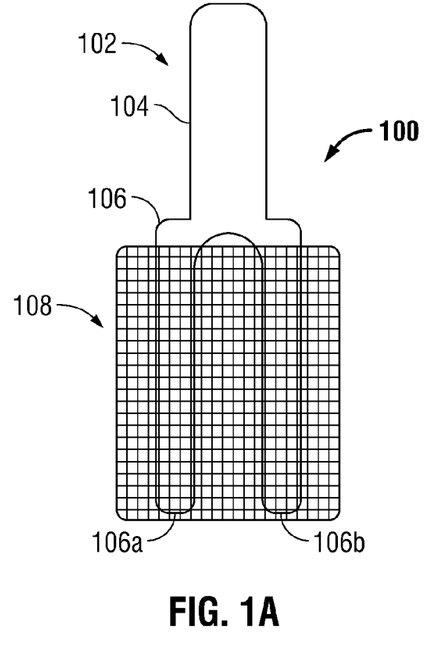
FIG. 1A illustrates a front plan view of an applicator of a wound closure device in accordance with an embodiment of the present disclosure.
Figure 1B:
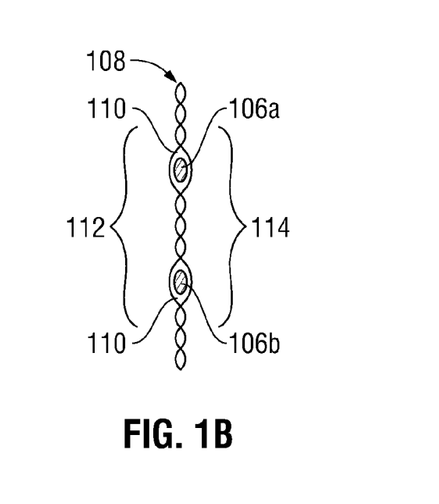
FIG. 1B illustrates a cross-sectional view of the applicator of the wound closure device of FIG. 1A.

Handle portion 104 and substrate engaging portion 106 may be monolithically formed or may be separate pieces which may be attached by various mechanical means as readily envisioned by those skilled in the art such that a variety of handle portion/substrate engaging portion configurations may be utilized.

A tissue fastening substrate 108 is adapted for releasable connection to the substrate engaging portion 106 of applicator 102. As illustrated in the present embodiment, substrate 108 is a mesh including pockets 110 in which tines 106a and 106b may be disposed. However, it is envisioned that any means for temporarily securing substrate 108 to substrate engaging portion 106 may be utilized, such as weaving the tines 106a and 106b through pores of the mesh. The areas of contact between the substrate engaging portion 106 and substrate 108 lack adhesive qualities so that the substrate 108 is readily removable.

While the substrate is illustrated and described in the current embodiment as a mesh, it is envisioned that other medical devices may be used with the wound closure device of the present disclosure including, but not limited to, patches, scaffolds, soft tissue repair devices, grafts, tapes, cables, slings, gauzes, buttresses, pledgets, tissue engineering scaffolds, wound dressings, drug delivery devices, tissue wraps, as well as other fasteners, implants, composite materials, and combinations thereof.

Substrate 108 is fabricated from any biocompatible material. Substrate 108 may be a biodegradable and/or non-biodegradable material which may be natural or synthetic. Substrates utilizing biodegradable materials enable quick and complete wound healing to occur, while non-biodegradable materials provides continuous reinforcement and support to the tissue.

Suitable synthetic biodegradable materials include but are not limited to polymers including aliphatic polyesters; polyamides; polyamines; polyalkylene oxalates; poly(anhydrides); polyamidoesters; copoly(ether-esters); poly(carbonates) including tyrosine derived carbonates; poly(hydroxyalkanoates) such as poly(hydroxybutyric acid), poly(hydroxyvaleric acid), and poly(hydroxybutyrate); 3-hydroxypropionate; polyimide carbonates; poly(imino carbonates) such as such as poly (bisphenol A-iminocarbonate) and the like; polyorthoesters; polyoxaesters including those containing amine groups; polyphosphazenes; poly(propylene fumarates); polyurethanes; dimethylsulfoniopropionate (DMSP); polymer drugs such as polydiflunisol, polyaspirin, and protein therapeutics; biologically modified (e.g., protein, peptide) bioabsorbable polymers; and copolymers, block copolymers, homopolymers, blends, and combinations thereof.

More specifically, aliphatic polyesters include, but are not limited to, homopolymers and copolymers of lactide (which includes lactic acid, D-,L- and meso lactide); glycolide (including glycolic acid); epsilon-caprolactone; p-dioxanone (1,4-dioxan-2-one); trimethylene carbonate(1,3-dioxan-2-one); alkyl derivatives of trimethylene carbonate; A-valerolactone; p-butyrolactone; y-butyrolactone; s-decalactone; hydroxybutyrate; hydroxyvalerate; 1,4-dioxepan-2-one (including its dimer 1,5,8,12-tetraoxacyclotetradecane-7,14-dione); 1,5-dioxepan-2-one; 6,6-dimethyl-1,4-dioxan-2-one; 2,5-diketomorpholine; pivalolactone; a, a diethylpropiolactone; ethylene carbonate; ethylene oxalate; 3-methyl-1,4-dioxane-2,5-dione; 3,3-diethyl-1,4-dioxan-2,5-dione; 6,8-dioxabicycloctane-7-one; and polymer blends and copolymers thereof.

Natural polymers may also be used in accordance with the present disclosure, non-limiting examples include, proteins such as collagen, gelatin, albumin, serum, and casein; poly (amino acids); polysaccharides such as cellulose (including carboxymethyl cellulose), dextran, chitin, chitosan, alginate and hyaluronic acid; glycosaminoglycans; gut; chemical derivatives thereof (substitutions and/or additions of chemical groups, for example, alkyl, alkylene, hydroxylations, oxidations, and other modifications routinely made by those skilled in the art); and copolymers and combinations thereof. Collagen as used herein includes natural collagen such as animal derived collagen, or synthetic collagen such as recombinant collagen. Additionally, natural materials include chemical modifications of the above-listed materials such as recombinant, aminated, sulfonated, and carboxylated polymer analogs.

Suitable non-biodegradable materials which may be useful in the present disclosure include but are not limited to fluorinated polymers such as fluoroethylenes and fluoroPEGs; polyolefins such as polyethylene (including ultra high molecular weight polyethylene (UHMWPE)) and polypropylene; polyesters such as poly ethylene terepththalate (PET); nylons; polyamides; polyurethanes; silicones; polybutesters; polyethylene glycols and polyethylene oxides; polyaryletherketone; copolymers and combinations thereof. Additionally, non-biodegradable polymers and monomers may be combined with each other and may also be combined with various biodegradable polymers and monomers to create the tissue fastening substrate of the present disclosure.

In some embodiments, hydrophilic polymers may be used. Suitable hydrophilic polymers include but are not limited to anionic, cationic and neutral monomers and polymers of vinyl polymers such as polyvinyl alcohol, polyvinyl methyl ether, polyvinylpyrrolidone (PVP), poly acrylic acid, styrene sulfonic acid, polyhydroxyethylmethylacrylate (pHEMA) and phospholipid vinyls; acrylic polymers such as sodium polyacrylate, polyethylacrylate, and polyacrylamide; polyethylene glycol, polypropylene oxide, and polypropylene glycol and homopolymers and copolymers thereof; phosphorylcholine functional acrylates and methacrylates; and homopolymers and copolymers thereof.

Substrate 108 may be non-porous, porous, or a combination thereof. In embodiments, a non-porous substrate may be a film. The term "porous" as used herein may define openings and spacings which are present as a surface characteristic or a bulk material property, partially or completely penetrating the medical device. Suitable materials for forming a porous substrate include, but are not limited to fibrous structures (e.g., knitted structures, woven structures, non-woven structures, etc.) and/or foams (e.g., open or closed cell foams). In embodiments, the pores may be in sufficient number and size so as to interconnect across the entire thickness of the substrate. Woven fabrics, kitted fabrics, and open cell foam are illustrative examples of structures in which the pores can be in sufficient number and size so as to interconnect across the entire thickness of the substrate.

In embodiments, the pores may not interconnect across the entire thickness of the substrate, but rather may be present at a portion thereof. Thus, in some embodiments, pores may be located on a portion of the substrate, with other portions of the substrate having a non-porous texture. Those skilled in the art reading the present disclosure will envision a variety of pore distribution patterns and configurations for the substrate. Closed cell foam or fused non-woven materials are illustrative examples of structures in which the pores may not interconnect across the entire thickness of the substrate.

Where the substrate is fibrous, the fibers may be filaments or threads suitable for knitting or weaving or may be staple fibers, such as those frequently used for preparing non-woven materials. Suitable techniques for making fibrous structures are within the purview of those skilled in the art.

Where the substrate is a foam, the pores may be formed using any method suitable to forming a foam or sponge including, but not limited to the lyophilization or freeze-drying of a composition. Suitable techniques for making foams are within the purview of those skilled in the art.

Pores may be created using methods within the purview of those skilled in the art, including but not limited to processes such as sintering, leaching of salt, sugar or starch crystals, and knitting or weaving of fibers.

In other embodiments, composite substrates are envisioned. For example, meshes may include one or more layers having a porous or non-porous construction. A non-porous layer may retard or prevent tissue ingrowth from surrounding tissues thereby acting as an adhesion barrier and preventing the formation of unwanted scar tissue while a porous layer may allow for tissue in-growth and integration.

Substrate 108 includes a tissue reactive surface 112 and a self-reactive surface 114. The tissue reactive surface 112 includes reactive groups for fixation of the substrate 108 to tissue "T" of wound "W" by crosslinking with reactive groups present in the tissue "T". The self-reactive surface 114 also includes reactive groups which have a complementary functionality with reactive groups of a self-reactive surface of a second substrate as described in detail below. By "complementary" it is meant that the reactive groups are able to specifically interact together to bond the self-reactive surfaces together. The term "bonding" as used herein refers to all types of chemical and physical crosslinking including covalent, ionic, and hydrophobic bonding. Chemical (covalent) crosslinking may be accomplished by any of a number of mechanisms, including free radical polymerization, condensation polymerization, anionic or cationic polymerization, step growth polymerization, electrophile-nucleophile reactions, combinations thereof, and the like. In addition, physical (non-covalent) crosslinks may result from complexation, hydrogen bonding, desolvation, Van der Waals interactions, ionic bonding, combinations thereof, and the like.

The tissue reactive surface 112 and/or the self-reactive surface 114 of substrate 108 may be functionalized by including one or more pendant functional groups suitable for reacting with tissue or a second self-reactive surface as described above.

In embodiments, the reactive groups are electrophilic or nucleophilic groups capable of reacting with tissue and/or each other to form a bond. Electrophilic functional groups include, for example, N-hydroxysuccinimides ("NHS"), sulfosuccinimides, carbonyldiimidazole, sulfonyl chloride, aryl halides, sulfosuccinimidyl esters, N-hydroxysuccinimidyl esters, succinimidyl esters such as succinimidyl succinates and/or succinimidyl propionates, isocyanates, thiocyanates, carbodiimides, benzotriazole carbonates, epoxides, aldehydes, maleimides, imidoesters, combinations thereof, and the like. In embodiments, the electrophilic reactive group is a succinimidyl ester.

Suitable nucleophilic groups include, but are not limited to, —$NH_2$, —SH, —OH, —$PH_2$, —CO—NH—$NH_2$ and combinations thereof. In embodiments, the nucleophilic reactive group is an amine.

In other embodiments, bonding may be accomplished with biological cross-linking systems, including for example, antibody/antigen; biotin/avidin; complementary peptide binding sequences; nucleotide base pairing and cross-linking; lock and key protein binding chemistry; self-assembling peptides; combinations thereof, and the like. In embodiments utilizing biotin and avidin reactive chemistries, biotin may be functionalized to include reactive groups such as amine, sulfhydryl, carbonyl, and carboxy, based upon the substrate to which it is to be bound. Avidin, streptavidin, and their derivatives, may be utilized for bonding with a substrate containing biotin or with endogenous biotin within tissue.

The material forming the substrate may be functionalized to provide reactive groups for binding or attaching to tissue or to another substrate. For example, amines may be provided on proteins, aminoglycans (such as chitosan, chondrotins, hyaluronic acid, and heparin), and polypeptides (like polylysine); carboxyl groups may be provided on proteins, polypeptides (like poly(glutamic acid)), polysaccharides (such as carboxylated dextran and carboxymethyl cellulose), and synthetic polymers (like carboxylated PEG and PEG-diadipate); hydroxyl groups may be provided on polysaccharides (like dextran), di-PEG adipate, and aliphatic polyesters (such as poly(lactic acid), poly(glycolic acid), poly(caprolactone), poly(trimethylene carbonate, poly(P-Dioxanone), and copolymers thereof); and thiols may be provided on some proteins. Alternatively, the substrates may be functionalized with tissue or substrate binding reactive groups, such as poly(lactic acid) and/or poly(glycolic acid), which include terminal carboxyl or hydroxyl groups.

The reactive groups may be positioned on or near the tissue reactive surface 112 and/or self-reactive surface 114 of substrate 108 using any suitable manner. For example, the substrate 108 may be formed from materials which naturally position reactive groups toward the outer surface of the substrate 108. In other examples, the substrate 108 may be surface-modified to covalently attach the reactive groups. In still other examples, the substrate 108 may be coated with an additional layer of material which includes the pendant reactive groups necessary to interact with the tissue and/or the second self-reactive surface as described herein.

Methods for coating substrates are within the purview of those skilled in the art, and include but are not limited to spraying, dipping, brushing, vapor deposition, co-extrusion, capillary wicking, film casting, molding, and the like. The reactive groups may be combined with the substrate in the form of a coating, film, foam, or powder on at least a portion of the tissue reactive and/or self-reactive surfaces of the substrate, in embodiments, on the entirety of the tissue reactive and/or self-reactive surfaces of the substrate.

In embodiments utilizing a coating, the coating process may include surface treatment of the substrate in order to promote adhesion of the coating to the tissue reactive surface and/or self-reactive surface of the substrate. The surfaces of the substrate can be treated using plasma, physical or chemical vapor deposition, pulsed laser ablation deposition, surface modification, or any other means within the purview of those skilled in the art to activate the tissue reactive or self-reactive surfaces of the substrate. In other embodiments, treatment may include the use of a primer such as a cross-linkable compound. In yet other embodiments, one or more deposition treatments could be used alone or in conjunction with the primer to achieve the desired association of coating with the tissue reactive and/or self-reactive surfaces of the substrate.

In embodiments, the tissue reactive surface 112 and/or self-reactive surface 114 may be functionalized by attaching a reactive component thereto. Suitable reactive components may include crosslinkers, adhesives, sealants, couplers, and the like that are functionalized with at least one reactive group capable of bonding the tissue reactive surface 112 to tissue "T" or the self-reactive surface 114 to the another self-reactive surface 114 as described above.

The tissue reactive surface 112 of substrate 108 may react with functional groups in tissue such as primary amine groups, secondary amine groups, hydroxyl groups, carboxylic groups, sulfonic groups and combinations thereof, and the like. In embodiments, the tissue reactive surface 112 of substrate 108 is an amine-reactive functional group which is capable of reacting with the free amines in tissue, thereby serving as a means for attaching substrate 108 to tissue "T". In embodiments, the tissue reactive surface 112 includes succinimidyl esters.

The self-reactive surface 114 of a first substrate 108 may including at least one reactive group 114a which is capable of reacting with the pendant reactive groups 114b of the self-reactive surface 114 of a second substrate 108. One reactive group may be an electrophile and the other may be a nucleophile. Electrophiles react with nucleophiles to form covalent bonds. Covalent crosslinks or bonds refer to chemical groups formed by reaction of functional groups on different materials that serve to covalently bind the different materials to each other. In certain embodiments, electrophilic reactive groups on a self-reactive surface of the first substrate may react with nucleophilic reactive groups on a self-reactive surface of the second substrate. When the self-reactive surfaces are joined together and mixed in an environment that permits reaction (e.g., physiological conditions within a wound), the electrophilic and nucleophilic reactive groups react with each other to form covalent bonds. In embodiments, the electrophilic reactive groups are succinimidyl esters and the nucleophilic reactive groups are amines.

The reactive groups may be protected prior to use of the wound closure device 100 by attaching a protective tape or releasable liner (not shown) to one or both surfaces 112, 114 of substrate 108. The protective tape or releasable liner may be removed prior to insertion of the substrate 108 into tissue "T". In embodiments, the protective tape or releasable liner may be fabricated from collagen, dextran, or any other natural or synthetic material which will not react with the reactive groups on the surface of the substrate to which it is applied.

Figure 2A:
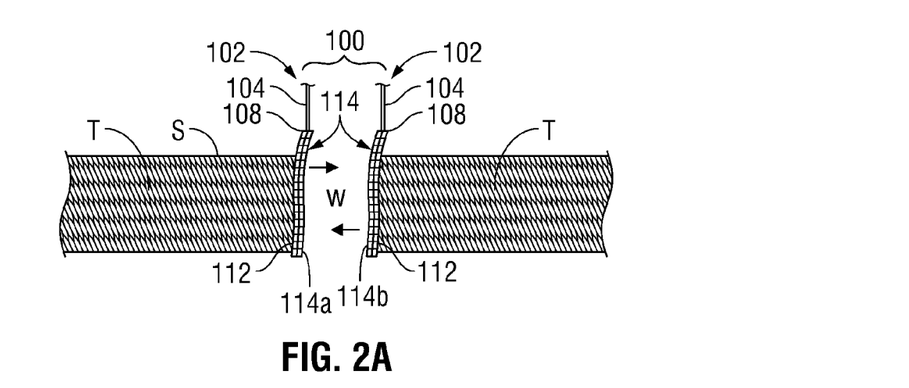
FIG. 2A schematically illustrates a wound closure device of the present disclosure placed within an open wound.

As illustrated in FIG. 2A, to effectuate the closing of a wound, substrates 108 of applicators 102 of wound closure device 100 are inserted into a wound "W". Handle portions 104 of applicators 102 are manipulated by a clinician such that the tissue reactive surfaces 112 of substrates 108 are pressed against each side of the tissue "T" within wound "W". The applicators 102 may be separately inserted into wound "W" to engage each substrate 108 with tissue "T" or the applicators 102 may be placed and manipulated within the wound "W" at the same time. Upon contact with the amine-containing tissue, the tissue reactive surfaces 112 react and fixate to tissue "T" within a useful time range. In embodiment, the reactive groups on tissue reactive surfaces 112 may be chemically "shielded" or "blocked" in aid of slowing the reaction with tissue "T" to allow for time to properly position and align the substrate with tissue "T". The handle portions 104 allow the clinician to apply even pressure to the tissue "T" in order to properly align the substrates 108 with the tissue "T" and thus, to uniformly bind the substrates 108 to the tissue "T" throughout the depth of the wound "W".

After the two tissue reactive surfaces 112 are sufficiently bound to the tissue "T", the clinician may move handle portions 104 of applicators 102 of wound closure device 100 in the direction of the arrows illustrated in FIG. 2A to appose and join the self-reactive surfaces 114 of the substrates 108. As the self-reactive surfaces 114 of the substrates 108 are pressed together, the reactive groups 114a, 114b on self-reactive surfaces 114 react such that the self-reactive surfaces adhere to each other. Thus, the self-reactive surfaces 114 crosslink upon contact with each other. The rate of crosslinking between the reactive groups 114a, 114b of the self-reactive surfaces 114 of the present disclosure may be tailored by controlling the concentration of the reactive groups 114a, 114b on the self-reactive surfaces 114. Generally, a faster cross-link time may be observed at a higher concentration of either of the reactive groups 114a, 114b of the self-reactive surfaces 114 than the rate observed for the same components at a lower concentration.

Figure 2B:
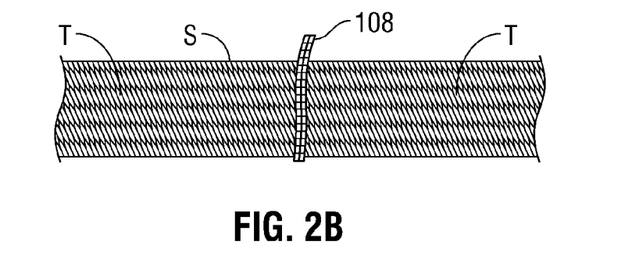
FIG. 2B schematically illustrates the wound closure device of FIG. 2A after closing the wound.

Thereafter, the applicators 102 may be removed from the substrates 108 thereby providing a closed wound as illustrated in FIG. 2B. As further illustrated in FIG. 2B, substrates 108 may extend out of surface "S" of tissue "T". The excess length of the substrates 108 may be trimmed at surface "S" of tissue "T", or just below surface "S" if cut prior to wound closure.

Thus, the wound closure device 100 may be used in a medical/surgical capacity in place of sutures, staples, adhesives, and other tissue fastening devices. The wound closure device 100 of the present disclosure thus has a number of advantageous properties. The tissue fastening substrates of the present disclosure are safe and biocompatible and possess enhanced adherence to tissue and to each other. The substrates crosslink to form a compliant tissue fastener which ensures stationary positioning of tissue edges in the desired location, evenly and uniformily along the length and depth of the wound therefore retaining the positional integrity of the aligned tissues. The reactive groups on the substrates form strong bonds such that the substrates exhibit excellent mechanical performance and strength while retaining the necessary pliability to adhere tissue. The strength and pliability allow a degree of movement of tissue without shifting the tissue edges.

Figure 3A:
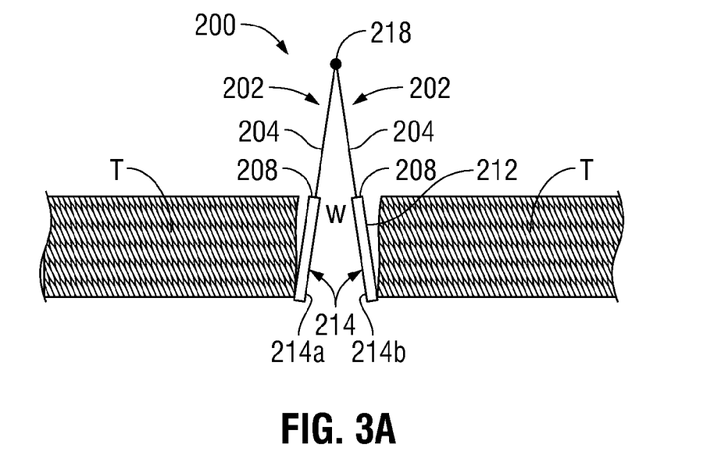
FIG. 3A schematically illustrates a wound closure device in accordance with another embodiment of the present disclosure placed within an open wound.
Figure 3B:
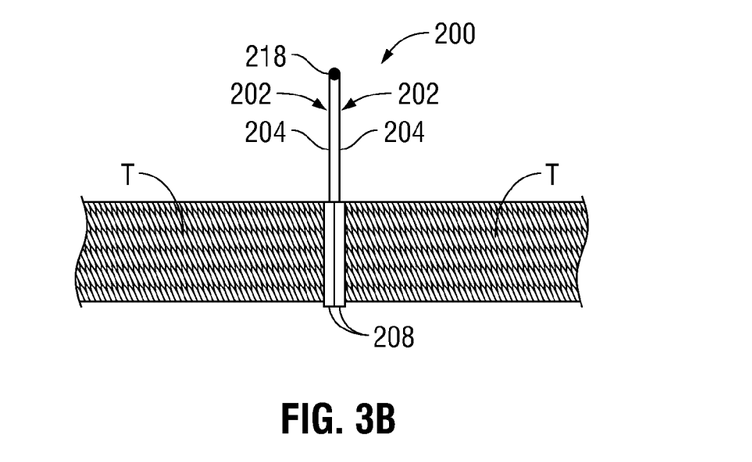
FIG. 3B schematically illustrates the wound closure device of FIG. 3A after closing the wound.
Figure 3C:
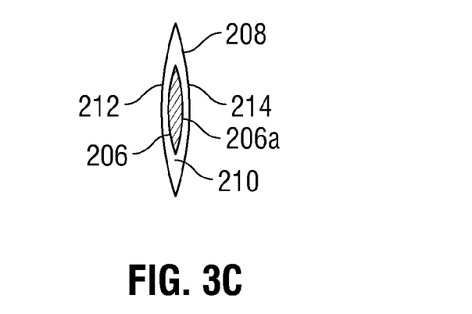
FIG. 3C illustrates a cross-sectional view of the wound closure device of FIGS. 3A-3B.

Another embodiment of a wound closure device 200 is illustrated in FIGS. 3A-3C. Wound closure device 200 includes applicators 202 joined via a hinge 218. Applicators 202 each include a handle portion 204 and a substrate engaging portion 206. Substrate 208, which is engaged with substrate engaging portion 206, is a non-porous film which includes a tissue reactive surface 212 and a self-reactive surface 214. As illustrated in the current embodiment, substrate engaging portion 206 includes a single tine 206a positioned within a sleeve or pocket 210 within substrate 208 for releasably securing the substrate 208 to the applicator 202.

The applicators 202 may be adapted to pivot relative to each other along the hinge 218 between an open position for positioning the tissue reactive surfaces 212 of the substrates 208 against tissue "T" (FIG. 3A) and a closed position for aligning tissue layers for apposing the self-reactive surfaces 214 of the substrates 208 thus, closing the wound (FIG. 3B).

In embodiments, the hinge 218 may be releasable for selective attachment of the applicators 202 with each other, thereby allowing the clinician to individually or jointly control the applicators 202. Hinge 218 may be any mechanical fastener which allows for pivotable movement, such as male/female fasteners, bayonet couplings, threaded connections, snap fit, friction fit, tongue and groove arrangements, and cam-lock mechanisms, for example.

In some embodiments, at least one bioactive agent may be combined with the tissue fastening substrate of the present disclosure. The term "bioactive agent", as used herein, is used in its broadest sense and includes any substance or mixture of substances that have clinical use. A bioactive agent could be any agent which provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. It is envisioned that the bioactive agent may be applied to the substrate in any suitable form of matter, e.g., films, powders, liquids, gels, combinations thereof, and the like.

The bioactive agent may be included on the tissue reactive surface, the self-reactive surface, or within the substrate. The bioactive agents may be incorporated into the substrate during formation of the substrate, such as by free suspension, liposomal delivery, microspheres, microparticles etc., or by coating a surface of the substrate, or portion thereof, such as by polymer coating, dry coating, and freeze drying. In some embodiments, bioactive agents may be incorporated within the pores of a porous substrate.

Examples of classes of bioactive agents which may be utilized in accordance with the present disclosure include antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of bioactive agents may be used with the substrates of the present disclosure.

Other bioactive agents which may be included as a bioactive agent in the substrate of the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g., oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; anticonvulsants; antidepressants; antihistamines; and immunological agents.

Additional examples of suitable bioactive agents include viruses and cells; peptides; polypeptides and proteins, as well as analogs, muteins, and active fragments thereof; immunoglobulins; antibodies; cytokines (e.g., lymphokines, monokines, chemokines); blood clotting factors; hemopoietic factors; interleukins (IL-2, IL-3, IL-4, IL-6); interferons (β-IFN, α-IFN and γ-IFN); erythropoietin; nucleases; tumor necrosis factor; colony stimulating factors (e.g., GCSF, GM-CSF, MCSF); insulin; anti-tumor agents and tumor suppressors; blood proteins; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); protein inhibitors; protein antagonists and protein agonists; nucleic acids such as antisense molecules, DNA, and RNA; oligonucleotides; and ribozymes.

The substrate may include a visualization agent and/or tactile indicator. In embodiments, the visualization agents may be utilized to improve the visibility of the substrate within a wound and/or to distinguish the tissue reactive surface 112 from the self-reactive surface 114. Visualization agents may be selected from a variety of nontoxic colored substances, such as dyes, suitable for use in implantable medical devices. Suitable dyes are within the purview of those skilled in the art and may include, for example, FD&C Blue #1, FD&C Blue #2, FD&C Blue #3, FD&C Blue #6, D&C Green #6, methylene blue, indocyanine green, other colored dyes, and combinations thereof. It is envisioned that additional visualization agents may be used such as fluorescent compounds (e.g., fluorescein or eosin), x-ray contrast agents (e.g., iodinated compounds), ultrasonic contrast agents, and MRI contrast agents (e.g., gadolinium containing compounds). In embodiments, either the tissue reactive surface or the self-reactive surfaces may be provided with a visualization agent to distinguish between the two surface. In other embodiments, the tissue reactive surface and the self-reactive surface each contain a different visualization agent to distinguish between the two surfaces.

Figure 4A:
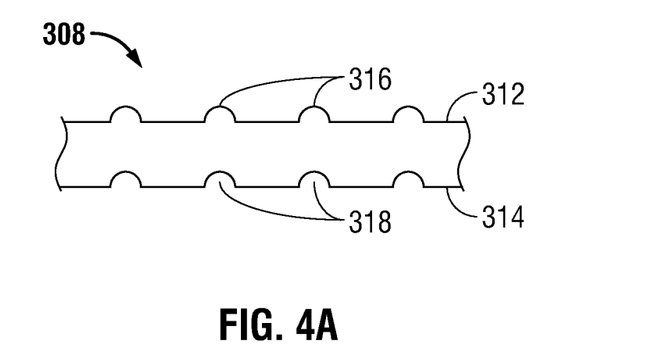
FIG. 4A illustrates a side view of a substrate including tactile indicators in accordance with an embodiment of the present disclosure.
Figure 4B:
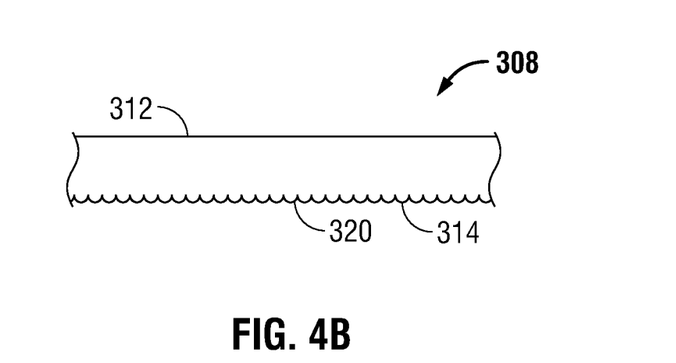
FIG. 4B illustrates a side view of a substrate including a tactile indicator in accordance with another embodiment of the present disclosure.

In embodiments, the tactile indicators may be utilized to tangibly distinguish the tissue reactive surface 112 from the self-reactive surface 114. The tissue reactive surface 112 and/or self-reactive surface 114 may include different surface topographies, such as differing textures or patterns of various shapes and sizes, to distinguish between the two surfaces. For example, as illustrated in FIG. 4A, the tissue reactive surface 312 of substrate 308 may include a first tactile indicator 316 and the self-reactive surface 314 may include a second tactile indicator 318 that is different from the first tactile indicator 316 of the tissue reactive surface 312. As illustrated, the first tactile indicator 316 includes protrusions and the second tactile indicator 318 includes indentations or recesses. In other embodiments, only one of the tissue reactive or self-reactive surfaces may include a tactile indicator. As illustrated in FIG. 4B, only the self-reactive surface 314 includes a tactile indicator 320 in the form of a textured surface.

Persons skilled in the art will understand that the devices and methods specifically described herein and illustrated in the accompanying figures are non-limiting exemplary embodiments, and that the description, disclosure, and figures should be construed merely exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another without departing from the scope of the present disclosure, and that such modifications and variations are also intended to be included within the scope of the present disclosure. Accordingly, the subject matter of the present disclosure is not to be limited by what has been particularly shown and described, except as indicated by the appended claims.

What is claimed is:

1. A wound closure device comprising:
   a first applicator including a handle portion and a substrate engaging portion;
   a second applicator including a handle portion and a substrate engaging portion;
   a first substrate releasably couplable to the substrate engaging portion of the first applicator, the first substrate including a tissue reactive surface and a self-reactive surface; and
   a second substrate releasably couplable to the substrate engaging portion of the second applicator, the second substrate including a tissue reactive surface and a self-reactive surface,
   wherein the self-reactive surfaces of the first and second substrates each possess reactive groups known to have complementary functionality for bonding the first and second substrates together.

2. The wound closure device of claim 1, wherein the substrate engaging portion of the first and second applicators each include at least one tine.

3. The wound closure device of claim 2, wherein the first and second substrates further include at least one pocket for engaging the at least one tine of the substrate engaging portions of the first and second substrates.

4. The wound closure device of claim 1, wherein the first and second substrates are non-porous, porous, or a composite thereof.

5. The wound closure device of claim 1, wherein the first and second substrates are a mesh.

6. The wound closure device of claim 1, wherein the tissue reactive surfaces of the first and second substrates include electrophilic reactive groups for binding with tissue.

7. The wound closure device of claim 1, wherein the tissue reactive surfaces of the first and second substrates include amine-reactive groups for binding with tissue.

8. The wound closure device of claim 1, wherein the tissue reactive surfaces of the first and second substrates include succinimidyl esters.

9. The wound closure device of claim 1, wherein one of the self-reactive surfaces of the first and second substrates includes electrophilic reactive groups and one of the self-reactive surfaces includes nucleophilic reactive groups.

10. The wound closure device of claim 9, wherein the electrophilic reactive groups are selected from the group consisting of N-hydroxysuccinimides, sulfosuccinimides, carbonyldiimidazole, sulfonyl chloride, aryl halides, sulfosuccinimidyl esters, N-hydroxysuccinimidyl esters, succinimidyl esters such as succinimidyl succinates and succinimidyl propionates, isocyanates, thiocyanates, carbodiimides, benzotriazole carbonates, epoxides, aldehydes, maleimides, imidoesters, and combinations thereof.

11. The wound closure device of claim 9, wherein the nucleophilic reactive groups are selected from the group consisting of —$NH_2$, —SH, —OH, —$PH_2$, —CO—NH—$NH_2$ and combinations thereof.

12. The wound closure device of claim 9, wherein the electrophilic reactive groups include succinimidyl esters and the nucleophilic groups include amines.

13. The wound closure device of claim 1, wherein the first applicator and the second applicator are hingedly connected.

14. The wound closure device of claim 1, wherein at least one of the first and second substrates includes a bioactive agent.

15. The wound closure device of claim 1, wherein at least one of the tissue reactive surfaces and the self-reactive surfaces of the first and second substrates includes a visualization agent, tactile indicator, or combination thereof.

16. A method for closing a wound comprising:
   introducing a first substrate including a tissue reactive surface and a self-reactive surface into a wound via a first applicator, the first applicator including a handle portion and a substrate engaging portion for releasably engaging the first substrate;
   introducing a second substrate including a tissue reactive surface and a self-reactive surface into a wound via a second applicator, the second applicator including a handle portion and a substrate engaging portion for releasably engaging the second substrate;
   applying the tissue reactive surfaces of the first and second substrates to tissue within a wound; and
   contacting the self-reactive surfaces of the first and second substrates.

17. The method of claim 16, further comprising the step of removing the first and second applicators after contacting the self-reactive surfaces of the first and second substrates.

18. The method of claim 17, further comprising the step of trimming portions of the substrates which extend out of a tissue surface after removing the first and second applicators.

19. The method of claim 16, wherein the step of applying the tissue reactive surfaces of the first and second substrates to tissue further comprises applying even pressure to the tissue for uniform binding of the tissue reactive surfaces with the tissue.

20. The method of claim 16, further comprising the step of aligning the first and second substrates prior to contacting the self-reactive surfaces of the first and second substrates.

* * * * *